(12) United States Patent
Chi et al.

(10) Patent No.: US 10,170,709 B2
(45) Date of Patent: Jan. 1, 2019

(54) PLATINUM COMPLEX HAVING CARBENE FRAGMENT, OLED USING THE SAME, AND NITROGEN-CONTAINING HETEROCYCLIC BIDENTATE CHELATE HAVING CARBENE UNIT

(71) Applicant: National Tsing Hua University, Hsinchu (TW)

(72) Inventors: Yun Chi, Hsinchu (TW); Che-Wei Hsu, Hsinchu (TW); Chung-Hao Tseng, Hsinchu (TW); Jia-Ling Liao, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 287 days.

(21) Appl. No.: 14/948,406

(22) Filed: Nov. 23, 2015

(65) Prior Publication Data
US 2017/0005279 A1    Jan. 5, 2017

(30) Foreign Application Priority Data
Jul. 3, 2015  (TW) .............................. 104121660 A (51) Int. Cl.
| | | |
|---|---|---|
| *H01L 51/00* | (2006.01) | |
| *C07F 15/00* | (2006.01) | |
| *C09K 11/06* | (2006.01) | |
| *C07D 401/04* | (2006.01) | |
| *C07D 403/04* | (2006.01) | |
| *H01L 51/50* | (2006.01) | |

(52) U.S. Cl.
CPC ........ *H01L 51/0087* (2013.01); *C07D 401/04* (2013.01); *C07D 403/04* (2013.01); *C07F 15/0086* (2013.01); *C09K 11/06* (2013.01); C09K 2211/1007 (2013.01); C09K 2211/1044 (2013.01); C09K 2211/1059 (2013.01); C09K 2211/185 (2013.01); H01L 51/5016 (2013.01)

(58) Field of Classification Search
CPC .................... H01L 51/0087; H01L 51/5016
See application file for complete search history.

(56) References Cited

U.S. PATENT DOCUMENTS

| | | | |
|---|---|---|---|
| 6,963,005 B2 | 11/2005 | Lecloux et al. | |
| 2009/0326237 A1 | 12/2009 | Strassner et al. | |
| 2010/0007273 A1* | 1/2010 | Djurovich ........... | H01L 51/0067 313/504 |
| 2014/0152637 A1 | 6/2014 | Fujita et al. | |

FOREIGN PATENT DOCUMENTS

| | | | |
|---|---|---|---|
| TW | 201229054 | | 7/2012 |
| WO | WO0215645 | * | 2/2000 |

OTHER PUBLICATIONS

Chi et al, Ruthenium and Osmium Complexes that Bear Functional Azolate Chelates for Dye-sensitized Solar Cells, Chemistry an Asian Journal, 2015.*
Agarwal et al., "Exploring the effect of axial ligand substitution (X = Br, NCS, CN) on the photodecomposition and electrochemical activity of [MnX(N-C)(CO)3] complexes," Dalton Transactions, Feb. 7, 2015, pp. 2212-2131.
Segarra et al., " Rhodium and Iridium Complexes with Chelating C-C'-Imidazolylidene-Pyridylidene Ligands: Systematic Approach to Normal, Abnormal, and Remote Coordination Modes," Organometallics, Jul. 5, 2012, pp. 5169-5176.
"Office Action of Taiwan Counterpart Application" , dated Jan. 25, 2016, p. 1-p. 6.
Chang et al., "Blue-Emitting Platinum(II) Complexes Bearing both Pyridylpyrazolate Chelate and Bridging Pyrazolate Ligands: Synthesis, Structures, and Photophysical Properties," Inorganic Chemistry, Nov. 21, 2007, pp. 11202-11212.
Martin Peters er al., "A simple synthesis of functionalized 3-methyl-1-pyridinyl-1H-imidazolium salts as bidentate N-heterocyclic-carbene precursors and their application in Ir-catalyzed arene borylation," Tetrahedron Letters, vol. 51, Issue 50, 2010, pp. 6622-6625.
Yong Cheng et al., "Synthesis, structures and catalytic activities of ruthenium(ii) carbonyl chloride complexes containing pyridine-functionalised N-heterocyclic carbenes," Dalton Transactions, Issue 35, 2009, pp. 7132-7140.
"Office Action of Taiwan Counterpart Application," dated Jul. 10, 2017, p. 1-p. 5.

* cited by examiner

*Primary Examiner* — Bethany L Martin
(74) *Attorney, Agent, or Firm* — JCIPRNET (57) ABSTRACT

A platinum complex having at least one carbene fragment, and an OLED using the same are described. The platinum complex contains a platinum cation, a zero-valent nitrogen-containing heterocyclic bidentate chelate, and a dianionic nitrogen-containing heterocyclic bidentate chelate. The zero-valent nitrogen-containing heterocyclic bidentate chelate has at least one carbene unit coordinating to platinum. The dianionic nitrogen-containing heterocyclic bidentate chelate has at least one electron-withdrawing substituent, and forms two N—Pt bonds, or one N—Pt bond and one C—Pt bond, with the central platinum cation.

6 Claims, 2 Drawing Sheets

PLATINUM COMPLEX HAVING CARBENE FRAGMENT, OLED USING THE SAME, AND NITROGEN-CONTAINING HETEROCYCLIC BIDENTATE CHELATE HAVING CARBENE UNIT

CROSS-REFERENCE TO RELATED APPLICATION

This application claims the priority benefit of Taiwan patent application serial no. 104121660, filed on Jul. 3, 2015. The entirety of the above-mentioned patent application is hereby incorporated by reference herein and made a part of this specification.

BACKGROUND OF THE INVENTION

Field of the Invention

The invention relates to a platinum complex for an organic light-emitting diode (OLED), and more particularly, to a platinum complex having a carbene fragment, an OLED using the platinum complex, and a nitrogen-containing heterocyclic bidentate chelate having a carbene unit that is for forming the platinum complex.

Description of Related Art

An organic electroluminescent apparatus generally contains an organic light-emitting diode (OLED) and a driving element. In the OLED, an organic material capable of emitting visible light after being excited is used as a light-emitting layer. The light-emitting layer usually includes a phosphorescent material, because such material can utilize a single-state exciton and a triple-state exciton at the same time to effectively increase the luminous efficiency of the OLED.

The blue-light luminous efficiency of known compounds having a maximum light-emitting wavelength of 470 to 530 nm is generally poor. For instance, U.S. Pat. No. 6,963,005 discloses a tetra-coordinated platinum (II) complex formed by chelating one O—O monoanionic bidentate chelate, one C—P monoanionic bidentate chelate, and one central platinum (II) ion. *Inorg. Chem.*, 2007, 11202—discloses a tetra-coordinated platinum (II) complex represented by the following formula (Y represents pyrazole or chlorine), and the solid quantum yield thereof can only reach up to 56%.

SUMMARY OF THE INVENTION

The invention provides a platinum complex having a carbene fragment. When used in the light-emitting layer of an OLED, the platinum complex having a carbene fragment can effectively increase the luminous efficiency of the OLED.

The invention also provides an OLED adopting the platinum complex.

The invention further provides a nitrogen-containing heterocyclic bidentate chelate having a carbene unit that is for forming the platinum complex.

The platinum complex having a carbene fragment contains a platinum cation, a zero-valent first nitrogen-containing heterocyclic bidentate chelate, and a dianionic second nitrogen-containing heterocyclic bidentate chelate. The first nitrogen-containing heterocyclic bidentate chelate has at least one carbene unit coordinating to platinum. The second nitrogen-containing heterocyclic bidentate chelate has at least one electron-withdrawing substituent, and forms two N—Pt bonds, or one N—Pt bond and one C—Pt bond, with the platinum cation.

In an embodiment of the invention, the platinum complex having a carbene fragment is represented by formula (I) or (II):

(I)

(II)

wherein X is CH or N, $R^F$ is $—C_mF_{2m+1}$, and m is an integer of 1 to 7.

In an embodiment of the invention, the first nitrogen-containing heterocyclic bidentate chelate is represented by formula (1), (2) or (3):

(1)

(2)

(3)

wherein R¹ is hydrogen, $C_{1-12}$ alkyl (namely alkyl having 1 to 12 carbons), unsubstituted phenyl, or a substituted phenyl group, each R² is independently $C_{1-6}$ alkyl (namely alkyl having 1 to 6 carbons), each R³ is independently hydrogen, $C_{1-12}$ alkyl, unsubstituted phenyl, or a substituted phenyl group, R⁴ is hydrogen or $C_{1-6}$ alkyl, and n is 1, 2 or 3, wherein any two adjacent R³ may join to form a ring.

The OLED of the invention includes two electrodes and a light-emitting layer disposed between the two electrodes, wherein the light-emitting layer contains the platinum complex having a carbene fragment.

The nitrogen-containing heterocyclic bidentate chelate having a carbene unit of an embodiment of the invention is represented by the above formula (1), (2) or (3).

In the platinum complex having a carbene fragment of the invention, the zero-valent first nitrogen-containing heterocyclic bidentate chelate has at least one carbene unit coordinating to platinum, and in addition to having higher-energy vacant orbitals and causing a blue shift to the emission wavelength, these carbene chelates can also increase the transition energy level of d-d orbitals of the central platinum atom, thus increasing the luminous efficiency. As a result, a blue-light or green-light material having high luminous efficiency is obtained.

In order to make the above features and advantages of the disclosure more comprehensible, embodiments accompanied with figures are described in detail below.

DESCRIPTION OF THE EMBODIMENTS

Some embodiments are provided below to further describe the invention, which are simply exemplary and are not intended to limit the scope of the invention.

[Platinum Complex Having a Carbene Fragment]

The platinum complex having a carbene fragment of the invention contains a platinum cation, a zero-valent first nitrogen-containing heterocyclic bidentate chelate, and a dianionic second nitrogen-containing heterocyclic bidentate chelate. The first nitrogen-containing heterocyclic bidentate chelate has at least one carbene unit coordinating to the platinum. The second nitrogen-containing heterocyclic bidentate chelate has at least one electron-withdrawing substituent, and forms two N—Pt bonds, or forms one N—Pt bond and one C—Pt bond, with the platinum cation.

The first nitrogen-containing heterocyclic bidentate chelate is, for instance, a bidentate chelate having one carbene unit represented by formula (1), a bidentate chelate having two carbene units represented by formula (2), or a bidentate chelate having two symmetric carbene units represented by formula (3).

(1)

(2)

(3)

In the formulas, R¹ is hydrogen, $C_{1-12}$ alkyl, unsubstituted phenyl, or a substituted phenyl group, each R² is independently $C_{1-6}$ alkyl, each R³ is independently hydrogen, $C_{1-12}$ alkyl, unsubstituted phenyl, or a substituted phenyl group, R⁴ is hydrogen or $C_{1-6}$ alkyl, and n is 1, 2 or 3, wherein any two adjacent R³ may join to form a ring.

The second nitrogen-containing heterocyclic bidentate chelate forming two N—Pt bonds with the platinum cation is, for instance, obtained by removing two protons from a nitrogen-containing heterocyclic compound (4') shown below, and may be represented by the following formula (4).

(4')

(4)

In the formulas, X is CH or N, $R^F$ is $—C_mF_{2m+1}$, and m is an integer of 1 to 7. Since the dianionic bidentate chelate contains a pyrazolyl group, and the fluoroalkyl group is an electron-withdrawing group, the HOMO energy level of the platinum complex can be more readily adjusted, such that the difference between the HOMO energy level and the LUMO energy level satisfies the phosphorescence of visible light that is emitted after excitation, thus making the complex applicable to OLED. In such case, the platinum complex having a carbene fragment can be represented by formula (I) or (II):

(I)

(II)

wherein the first nitrogen-containing heterocyclic bidentate chelate having one carbene unit in formula (I) is, for instance, represented by the above formula (1), and the first nitrogen-containing heterocyclic bidentate chelate having two carbene units in formula (II) is, for instance, represented by the above formula (2) or (3).

Some practical examples of the platinum complex having a carbene fragment that satisfy formula (I) and contain the first nitrogen-containing heterocyclic bidentate chelate of formula (1) are the following platinum complexes represented by formulas (I-1-1), (I-1-2), (I-1-3), (I-1-4), (I-1-5) and (I-1-6), respectively, abbreviated as compounds (I-1-1), (I-1-2), . . . hereinafter. The abbreviation rule also applies to the later described platinum complexes represented by other chemical structures.

(I-1-1)

(I-1-2)

(I-1-3)

(I-1-4)

(I-1-5)

(I-1-6)

Some practical examples of the platinum complex having a carbene fragment that satisfy formula (II) and contain the first nitrogen-containing heterocyclic bidentate chelate of formula (2) are the platinum complexes represented by formulas (II-2-1), (II-2-2), (II-2-3), (II-2-4), (II-2-5), (II-2-6), (II-2-7), (II-2-8), (II-2-9) and (II-2-10), respectively.

(II-2-1)

(II-2-2)

(II-2-3)

(II-2-4)

(II-2-5)

(II-2-6)

(II-2-7)

(II-2-8)

(II-2-9)

(II-2-10)

Some practical examples of the platinum complex having a carbene fragment that satisfy formula (II) and contain the first nitrogen-containing heterocyclic bidentate chelate of formula (3) are the following platinum complexes represented by formulas (II-3-1), (II-3-2), (II-3-3), (II-3-4), (II-3-5) and (II-3-6), respectively.

(II-3-1)

(II-3-2)

(II-3-3)

(II-3-4)

(II-3-5)

(II-3-6)

Some practical examples of the platinum complex having a carbene fragment, in which the second nitrogen-containing heterocyclic bidentate chelate is not a chelate represented by formula (4), are the following platinum complexes represented by formulas (III-2-1), (III-3-1) and (II-3-2), respectively.

(III-2-1)

(III-3-1)

(III-3-2)

Among them, compound (III-2-1) is closer to compound (II-2-1), compound (III-3-1) is closer to compound (II-3-3), and compound (III-3-2) is closer to compound (II-3-5).

The OLED of the invention includes two electrodes and a light-emitting layer disposed therebetween. The light-emitting layer contains the above platinum complex having a carbene fragment. The material of each of the two electrodes can be selected from commonly used materials in the field, and other functional layers can also be disposed between each electrode and the light-emitting layer using a known technique in the art.

[Forming Method of Platinum Complex having a Carbene Fragment]

The first nitrogen-containing heterocyclic bidentate chelate is formed, for example, after a precursor thereof reacts with a platinum source. The precursor of the first nitrogen-containing heterocyclic bidentate chelate is formed, for example, by mixing and reacting a compound having a corresponding ring structure and a required reagent.

For instance, the precursors of two examples of the first heterocyclic bidentate chelate represented by formula (1) can be formed by, for instance, the following steps.

Examples of the case where the first nitrogen-containing heterocyclic bidentate chelate is bonded to the platinum atom first are shown below.

The platinum complex having a carbene fragment of the invention can be prepared by adopting suitable reactants and reaction conditions according to the change of each chelate, and the reaction preparation method can be modified based on a known technique in the art. A specific example of the preparation method of the platinum complex contains the following steps. The precursor of the first nitrogen-containing heterocyclic bidentate chelate having a carbene unit, a platinum source, and other required reagent(s) are mixed, and then the obtained product, the precursor (such as a compound of formula (4')) of the $2^{nd}$ nitrogen-containing heterocyclic bidentate chelate, and other required reagent(s) are mixed, and a reaction was caused by heating. The order in which the first and the second nitrogen-containing heterocyclic bidentate chelates are bonded to the platinum atom can be reversed. That is, the platinum atom and the precursor of the second nitrogen-containing heterocyclic bidentate chelate are reacted first, and then the product and the precursor of the first nitrogen-containing heterocyclic bidentate chelate are reacted.

EXAMPLES

Certain examples are provided below to further describe the invention, which are merely exemplary and are not intended to limit the scope of the invention.

Example 1

Preparation of Compound (I-1-1):

(I-1-1)

300 mg (0.71 mmol) of Pt(DMSO)$_2$Cl$_2$, 228 mg (0.75 mmol) of 1-methyl-3-(2-pyridyl)imidazolium hexafluorophosphate, and 120 mg (1.42 mmol) of sodium bicarbonate were placed in a two-necked bottle, and the reactants were reacted at a reaction temperature controlled at 120° C. for 19 hours by using 10 mL of anhydrous dimethyl sulfoxide as a solvent. Then, the temperature was lowered back to room temperature, 203 mg (0.75 mmol) of 5,5'-bis(trifluoromethyl)-2H,2'H-3,3'-bipyrazole and 117 mg (1.42 mmol) of sodium acetate were added, and then the mixture was reacted at 120° C. for 12 hours. After the reaction was complete, deionized water was added for washing and filtering, and the filtered substance was collected. After sublimation, 210 mg of a product was obtained, with a yield of 45%.

Spectrum data of compound (I-1-1): MS (FAB, $^{195}$Pt): m/z 622 [M$^+$]; $^1$H NMR (400 MHz, d$_6$-DMSO, 294K): δ 10.68 (br, 1H), 8.35 (br, 2H), 8.08 (br, 1H), 7.64 (br, 1H), 7.57 (br, 1H), 6.65 (br, 1H), 6.59 (br, 1H), 4.45 (s, 3H); $^{19}$F NMR (376 MHz, d$_6$-DMSO, 294K): δ-58.87 (s, 3F), −59.34 (s, 3F).

Example 2

Preparation of Compound (I-1-3):

(I-1-3)

Except that the starting reactants were different, the synthesis steps were similar to those of compound (I-1-1), with a yield of 40%.

Spectrum data of compound (I-1-3): MS (FAB, $^{195}$Pt): m/z 678 [M$^+$]; $^1$H NMR (400 MHz, d$_6$-acetone 294K): δ 10.52 (d, J=6.3 Hz, 1H), 8.47 (s, 1H), 8.02 (s, 1H), 7.65 (d, J=6.3 Hz, 1H), 7.56 (s, 1H), 6.63 (s, 1H), 6.56 (s, 1H), 4.41 (s, 3H), 1.37 (s, 9H); $^{19}$F NMR (376 MHz, d$_6$-acetone, 294K): δ −58.83 (s, 3F), −59.31 (s, 3F).

Example 3

Preparation of compound (I-1-5):

(I-1-5)

Except that the starting reactants were different, the synthesis steps were similar to those of compound (I-1-1), with a yield of 40%.

Spectrum data of compound (I-1-5): MS (FAB, $^{195}$Pt): m/z 706 [M$^+$]; $^1$H NMR (400 MHz, d$_6$-acetone, 294K): δ 10.82 (d, J=6.3 Hz, 1H), 8.30 (s, 1H), 8.00 (s, 1H), 7.73 (s, 1H), 7.59 (d, J=6.3 Hz, 1H), 7.18 to 7.08 (m, 1H), 6.60 (s, 1H), 6.54 (s, 1H), 1.51 (d, J=6.64 Hz, 6H), 1.46 (s, 9H); $^{19}$F NMR (376 MHz, d$_6$-acetone, 294K): δ −69.24 (s, 3F), −71.13 (s, 3F).

Figure 1:
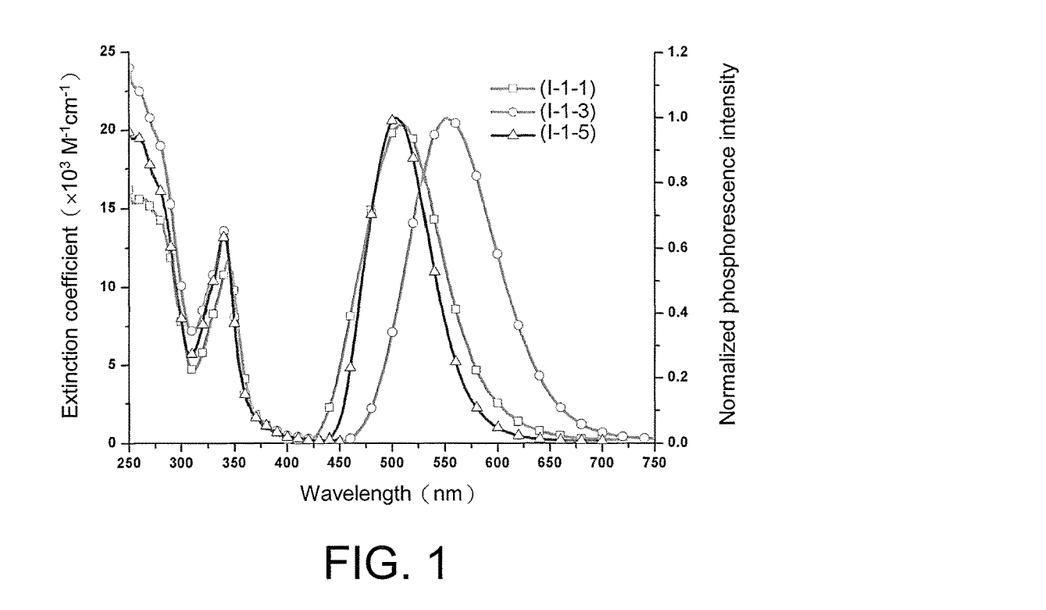
FIG. 1 shows the absorption spectra and the phosphorescence spectra of the platinum complexes having one carbene fragment that were synthesized in Examples 1 to 3 of the invention.

The absorption spectra and the phosphorescence spectra of the platinum complexes having one carbene fragment that were synthesized in Examples 1 to 3 are shown in FIG. 1, and the absorption peak location (abs λ$_{max}$), the emission peak location (em λ$_{max}$), the quantum yield (φ), and the phosphorescence lifetime (τ) thereof are listed in Table 1 below.

TABLE 1

| Compound | abs λ$_{max}$$^a$ (nm) | em λ$_{max}$$^b$ (nm) | φ$^b$ (%) | τ$^b$ (ns) |
|---|---|---|---|---|
| (I-1-1) | 279, 365 | 510 | 84.4 | 1126 |
| (I-1-3) | 280, 340 | 552 | 93.8 | 780 |
| (I-1-5) | 280, 340 | 501 | 94.7 | 1022 |

$^a$UV/visible light spectra were measured in a CH$_2$Cl$_2$ solution.
$^b$Phosphorescence characteristics were measured in a powder state.

It is clear from FIG. 1 and Table 1 that the three compounds all have a high luminous efficiency approximately between 85% and 95%, and the phosphorescence lifetime thereof shorter than that of the general phosphorescent compound helps to reduce the occurrence of triple-state quenching, thus increasing the luminous efficiency of an OLED. Moreover, by the alkyl modification on compound (I-1-5), sublimability of the molecules can be effectively increased facilitating the manufacture of an element.

Example 4

Preparation of compound (II-2-1):

100 mg (0.23 mmol) of Pt(DMSO)$_2$Cl$_2$, 111 mg (0.24 mmol) of [1-(3'-(1'-methylpyridiniumyl)-3-methyl]-imidazolium bishexafluorophosphate, and 40 mg (0.48 mmol) of sodium bicarbonate were placed in a two-necked flask, and the reactants were reacted at a reaction temperature controlled at 110° C. using 4 mL of anhydrous dimethyl sulfoxide as a solvent. After reacting for 12 hours, the temperature was lowered back to room temperature, 70.4 mg (0.26 mmol) of 5,5'-bis(trifluoromethyl)-2H,2'H-3,3'-bipyrazole was added, and then the mixture was reacted at 110° C. for 12 hours. After the reaction was complete, the solvent was removed with a vacuum system, and column chromatographic separation was performed by using ethyl acetate as an eluent, and then recrystallization was performed using dichloromethane to obtain 92 mg of a product with a yield of 61%.

Spectrum data of compound (II-2-1): MS (FAB, $^{195}$Pt): m/z 636 [M$^+$]; $^1$H NMR (400 MHz, d$_6$-DMSO, 298K): δ 8.60 (d, J=6.2 Hz, 1H), 8.26 to 8.25 (br, 2H), 7.73 (dd, J=6.5 Hz, J=7.7 Hz, 1H), 7.55 (d, J=2 Hz, 1H), 6.60 (s, 1H), 6.56 (s, 1H), 4.69 (s, 3H), 4.48 (s, 3H); $^{19}$F NMR (376 MHz, d$_6$-DMSO, 298 K): δ −58.88 (s, CF$_3$), −58.94 (s, CF$_3$).

Example 5

Preparation of Compound (III-2-1):

Except that the starting reactants and the second nitrogen-containing heterocyclic bidentate chelate (and the reaction precursor thereof) were different, the synthesis steps were similar to those of compound (II-2-1), with a yield of 69%.

Spectrum data of compound (III-2-1): MS (FAB, $^{195}$Pt): m/z 679 [M+1$^1$]; $^1$H NMR (400 MHz, d$_6$-DMSO, 298K): δ 8.46 (d, J=6.2 Hz, 1H), 8.26 (d, J=2 Hz, 1H), 8.24 (d, J=7.92 Hz, 1H) 7.69 (dd, J=6.5 Hz, J=7.6 Hz, 1H), 7.53 (d, J=1.92 Hz, 1H), 6.27 (s, 1H), 6.26 (s, 1H), 3.87 (s, 3H), 3.66 (s, 3H), 1.88 (s, 6H); $^{19}$F NMR (376 MHz, d$_6$-DMSO, 298 K): δ −58.48 (s, 2×CF$_3$).

Example 6

Preparation of Compound (II-2-3):

Except that the starting reactants were different, the synthesis steps were similar to those of compound (II-2-1), with a yield of 58%.

Spectrum data of compound (II-2-3): MS (FAB, $^{195}$Pt): m/z 737 [M$^+$]; $^1$H NMR (400 MHz, d$_6$-DMSO, 298K): δ 8.61 (d, J=6 Hz, 1H), 8.26 to 8.24 (br, 2H), 7.72 (dd, J=6.4 Hz, J=8 Hz, 1H), 7.54 (d, J=2 Hz, 1H), 6.66 (s, 1H), 6.61 (s, 1H), 4.68 (s, 3H), 4.45 (s, 3H); $^{19}$F NMR (376 MHz, d$_6$-DMSO, 298 K): δ −83.20 (d, J=56.4 Hz, CF$_3$).

Example 7

Preparation of Compound (II-2-5):

Except that the starting reactants were different, the synthesis steps were similar to those of compound (II-2-1), with a yield of 64%.

Spectrum data of compound (II-2-5): MS (FAB, $^{195}$Pt): m/z 650 [M$^+$]; $^1$H NMR (400 MHz, d$_6$-DMSO, 298K): δ 15.86 (br, 1H), 8.68 (t, J=5.84 Hz, 1H), 8.35 (d, J=7.96 Hz, 1H), 8.30 (d, J=2.08 Hz, 1H), 7.88 (d, J=2.12 Hz, 1H), 7.69 (t, J=6.76 Hz, 1H), 6.88 (m, 1H), 6.78 (s, 1H), 6.69 (s, 1H), 1.48 (d, J=6.6 Hz, 6H); $^{19}$F NMR (376 MHz, d$_6$-DMSO, 298 K): δ −59.03 (s, CF$_3$), −59.28 (s, CF$_3$).

Example 8

Preparation of Compound (II-2-7):

(II-2-7)

Except that the starting reactants were different, the synthesis steps were similar to those of compound (II-2-1), with a yield of 59%.

Spectrum data of compound (II-2-7): MS (FAB, $^{195}$Pt): m/z 637 [M+1$^+$]; $^1$H NMR (400 MHz, d$_6$-DMSO, 298K): δ 15.91 (br, 1H), 8.65 (t, J=5.88 Hz, 1H), 8.33 (d, J=7.88 Hz, 1H), 8.23 (d, J=2.08 Hz, 1H), 7.70 to 7.67 (br, 2H), 6.76 (s, 1H), 6.67 (s, 1H), 5.15 (q, J=7.04 Hz, 2H), 1.39 (t, J=7 Hz, 3H); $^{19}$F NMR (376 MHz, d$_6$-DMSO, 298 K): δ −59.00 (s, CF$_3$), −59.06 (s, CF$_3$).

Example 9

Preparation of compound (II-2-9):

(II-2-9)

Except that the starting reactants were different, the synthesis steps were similar to those of compound (II-2-1), with a yield of 55%.

Spectrum data of compound (II-2-9): MS (FAB, $^{195}$Pt): m/z 736 [M$^+$]; $^1$H NMR (400 MHz, d$_6$-DMSO, 298K): δ 15.91 (br, 1H), 8.53 (s, 1H), 8.29 (d, J=7.64 Hz, 1H), 8.18 (s, 1H), 7.65 to 7.67 (br, 2H), 6.82 (s, 1H), 6.74 (s, 1H), 5.15 (q, J=6.88 Hz, 2H), 1.35 (t, J=7 Hz, 3H); $^{19}$F NMR (376 MHz, d$_6$-DMSO, 298 K): δ −83.14 (d, J=86.8 Hz, CF$_3$), −108.41 (d, J=376.92 Hz, CF$_2$).

Figure 2:
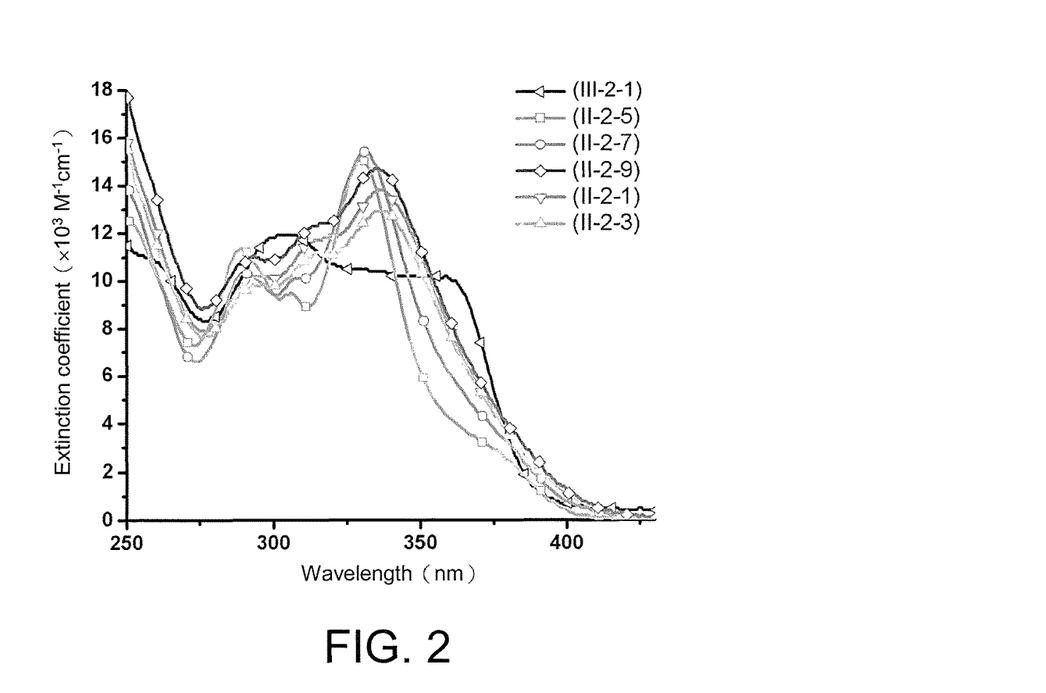
FIG. 2 shows the absorption spectra of the platinum complexes having two carbene fragments that were synthesized in Examples 4 to 9 of the invention.
Figure 3:
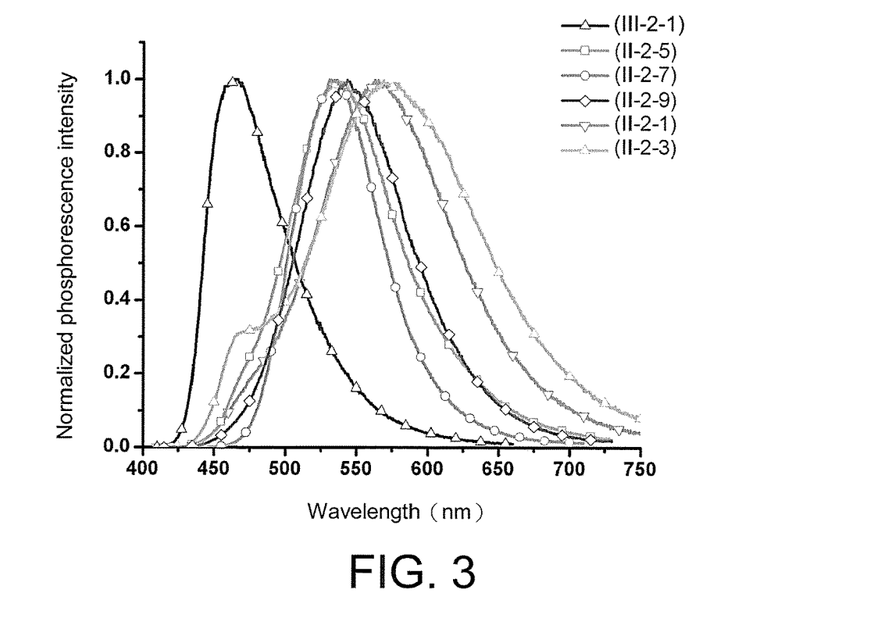
FIG. 3 shows the phosphorescence spectra of the platinum complexes having two carbene fragments that were synthesized in Examples 4 to 9 of the invention.

The absorption spectra of the platinum complexes having two carbene fragments that were synthesized in Examples 4 to 9 are shown in FIG. 2, the phosphorescence spectra thereof are shown in FIG. 3, and the absorption peak location (abs λ$_{max}$) the emission peak location (em λ$_{max}$), the quantum yield (φ), and the phosphorescence lifetime (τ) thereof are listed in Table 2 below.

TABLE 2

| Compound | abs λ$_{max}$$^a$ (nm) | em λ$_{max}$$^b$ (nm) | φ$^b$ (%) | τ$^b$ (ns) |
| --- | --- | --- | --- | --- |
| (II-2-1) | 291, 312, 336 | 565 | 89 | 1247 |
| (III-2-1) | 306, 337, 359 | 462 | 16.2 | 7692 |
| (II-2-3) | 293, 315, 336 | 569 | 24 | 1520 |
| (II-2-5) | 289, 330 | 535 | 78 | 883 |
| (II-2-7) | 290, 331 | 532 | 96 | 852 |
| (II-2-9) | 293, 316, 335 | 543 | 99 | 841 |

$^a$UV/visible light spectra were measured in a CH$_2$Cl$_2$ solution.
$^b$Phosphorescence characteristics were measured in a powder state.

It is clear from FIGS. 2 and 3 and Table 2 that most of these compounds have a good luminous efficiency, and the structure having an intra-molecular hydrogen bond can increase the molecular rigidity and increase the luminescence quantum yield of the compounds up to 99%. Moreover, the phosphorescence lifetime thereof shorter than that of the general phosphorescent compound helps to reduce the occurrence of triple-state quenching, thus increasing the luminescent efficiency of an OLED.

Example 10

Preparation of Compound (II-3-1):

(II-3-1)

300 mg (0.71 mmol) of Pt(DMSO)$_2$Cl$_2$, 351 mg (0.75 mmol) of 1,1'-dimethyl-3,3'-methylene-diimidazolium bishexafluorophosphate, and 120 mg (1.42 mmol) of sodium bicarbonate were placed in a two-necked flask, and then the reactants were reacted at a temperature controlled at 120° C. for 19 hours using 10 mL of anhydrous dimethyl sulfoxide as a solvent. Then, the temperature was lowered back to room temperature, 203 mg (0.75 mmol) of 5,5'-bis(trifluoromethyl)-2H,2'H-3,3'-bipyrazole was added, and then the mixture was reacted at 120° C. for 12 hours. After the reaction was complete, the solvent was removed with a vacuum system, and column chromatographic separation was performed using ethyl acetate/acetone (20:1) as an eluent, and then recrystallization was performed using a mixed solution of ethyl acetate and hexane to obtain 297 mg of a product with a yield of 65%.

Spectrum data of compound (II-3-1): MS (FAB, $^{195}$Pt): m/z 639 [M$^+$]; $^1$H NMR (500 MHz, d$_6$-DMSO, 294K): δ 7.64 (d, J=2.0 Hz, 2H), 7.46 (d, J=2.0 Hz, 2H), 6.52 (s, 2H), 6.20 (d, J=13.0 Hz, 1H), 6.10 (d, J=13.0 Hz, 1H), 3.97 (s, 6H); $^{19}$F NMR (470 MHz, d$_6$-DMSO, 294K): δ −59.11 (s, 6F).

Example 11

Preparation of Compound (II-3-3):

(II-3-3)

Except that the starting reactants were different, the synthesis steps were similar to those of compound (II-3-1), with a yield of 70%.

Spectrum data of compound (II-3-3): (FAB, $^{195}$Pt): m/z 695 [M$^+$]; $^1$H NMR (500 MHz, d$_6$-DMSO, 294K): δ 7.65 (d, J=2.0 Hz, 2H), 7.64 (d, J=2.0 Hz, 2H), 6.53 (s, 2H), 6.18 (d, J=13.5 Hz, 1H), 6.09 (d, J=13.5 Hz, 1H), 5.32 (m, J=6.5 Hz, 2H), 1.60 (d, J=6.5 Hz, 6H), 1.15 (d, J=6.5 Hz, 6H); $^{19}$F NMR (470 MHz, d$_6$-DMSO, 294K): δ −59.25 (s, 6F).

Example 12

Preparation of Compound (III-3-1):

(III-3-1)

Except that the starting reactants and the second nitrogen-containing heterocyclic bidentate chelate (and the reaction precursor thereof) were different, the synthesis steps were similar to those of compound (II-3-1), with a yield of 48%.

Spectrum data of compound (III-3-1): MS (FAB, $^{195}$Pt): m/z 649 [M$^+$]; $^1$H NMR (500 MHz, d$_6$-DMSO, 294K): δ 7.62 (d, J=2.5 Hz, 1H), 7.58 (d, J=2.0 Hz, 1H), 7.48 (d, J=2.5 Hz, 1H), 7.42 (d, J=7.5 Hz, 1H), 7.37 (d, J=2.0 Hz, 1H), 7.33 (s, 1H), 7.23 (d, J=7.5 Hz, 1H), 6.60 (s, 1H), 6.15 (d, J=13.0 Hz, 1H), 6.00 (d, J=13.0 Hz, 1H), 3.99 (s, 3H), 3.70 (s, 3H); $^{19}$F NMR (470 MHz, d$_6$-DMSO, 294K): δ −59.00 (s, 3F), −60.77 (s, 3F).

Example 13

Preparation of Compound (II-3-5):

(II-3-5)

Except that the starting reactants were different, the synthesis steps were similar to those of compound (II-3-1), with a yield of 58%.

Spectrum data of compound (II-3-5): MS (FAB, $^{195}$Pt): m/z 723 [M$^+$]; $^1$H NMR (400 MHz, d$_6$-DMSO, 294K): δ 7.50 (d, J=1.5 Hz, 2H), 7.40 (d, J=1.5 Hz, 2H), 6.48 (s, 2H), 5.26 (sp, J=6.5 Hz, 2H), 4.72 (dd, J=14.5, 11 Hz, 2H), 4.32 (dd, J=14.5, 6 Hz, 2H), 2.33 to 2.28 (m, 1H), 1.88 to 1.80 (m, 1H), 1.38 (d, J=6.5 Hz, 6H), 1.35 (d, J=6.5 Hz, 6H); $^{19}$F NMR (470 MHz, d$_6$-DMSO, 294K): δ −58.87 (s, 6F).

Example 14

Preparation of Compound (III-3-2):

(III-3-2)

Except that the starting reactants and the second nitrogen-containing heterocyclic bidentate chelate (and the reaction precursor thereof) were different, the synthesis steps were similar to those of compound (II-3-1), with a yield of 63%.

Spectrum data of compound (III-3-2): MS (FAB, $^{195}$Pt): m/z 733 [M$^+$]; $^1$H NMR (500 MHz, d$_6$-DMSO, 294K): (δ 7.50 (d, J=2.0 Hz, 1H), 7.42 to 7.37 (m, 3H), 7.32 (d, J=2.0 Hz, 1H), 7.19 (d, J=7.5 Hz, 1H), 6.57 (s, 2H), 5.21 (sp, J=6.5 Hz, 1H), 5.11 (sp, J=6.5 Hz, 1H), 4.69 (dd, J=14.0, 11.0 Hz, 1H), 4.57 (dd, J=14.0, 11.0 Hz, 1H), 4.31 to 4.21 (m, 2H), 2.32 to 2.25 (m, 1H), 1.84 to 1.76 (m, 1H), 1.44 (d, J=6.5 Hz, 3H), 1.33 (d, J=6.5 Hz, 3H), 1.29 (d, J=6.5 Hz, 3H), 1.24 (d, J=6.5 Hz, 3H); $^{19}$F NMR (470 MHz, d$_6$-DMSO, 294K): δ −58.72 (s, 3F), −60.83 (s, 2F).

Figure 4:
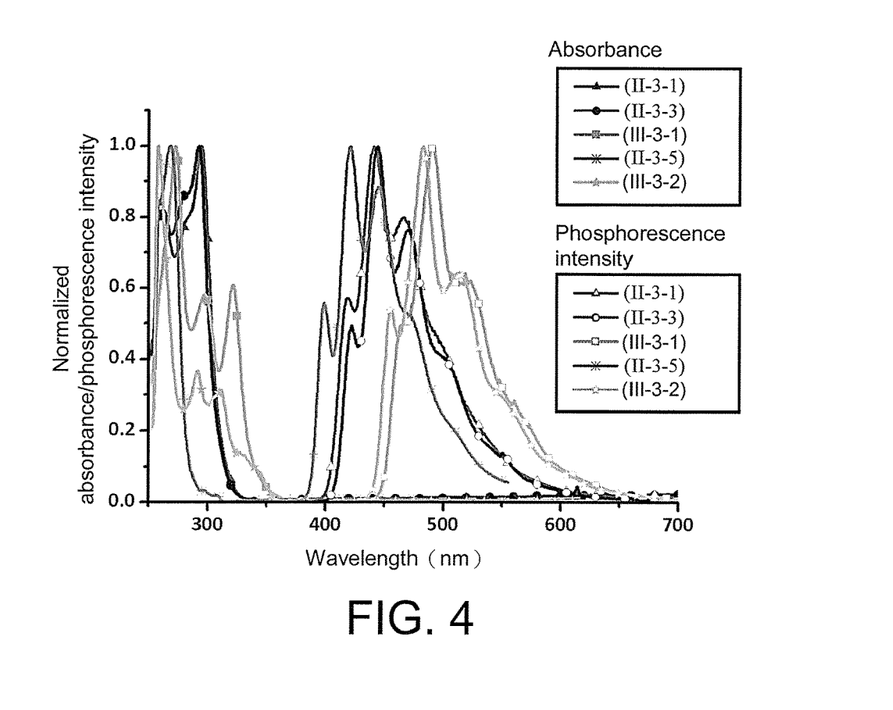
FIG. 4 shows the absorption spectra and the phosphorescence spectra of the platinum complexes having two carbene fragments that were synthesized in Examples 10 to 14 of the invention.

The absorption spectra and the phosphorescence spectra of the platinum complexes having two carbene fragments that were synthesized in Examples 10 to 14 are shown in FIG. 4, and the absorption peak location (abs λ$_{max}$), the emission peak location (em λ$_{max}$), the quantum yield (φ), and the phosphorescence lifetime (z) thereof are listed in Table 3 below.

TABLE 3

| | abs $\lambda_{max}{}^a$ (nm) | em $\lambda_{max}{}^b$ (nm) | $\phi^b$ (%) | $\tau^b$ (μs) |
|---|---|---|---|---|
| (II-3-1) | 263, 280, 294 | 418, 441, 466 | 50 | 29 |
| (II-3-3) | 262, 279, 292 | 422, 444, 470 | 50 | 33 |
| (III-3-1) | 273, 298, 321 | 464, 491, 520 | 96 | 22 |
| (II-3-5) | 268 | 398, 421, 446 | 70 | 21, 46 |
| (III-3-2) | 258, 290, 312, 330 | 455, 482, 514 | 100 | 41 |

$^a$ UV/visible light spectra were measured in a dimethyl sulfoxide solution.
$^b$ Phosphorescence characteristics were measured in a powder state.

It is clear from FIG. 4 and Table 3 that, these compounds have good blue-light luminous properties, wherein (III-3-2) and (III-3-1) not only show the performance of a blue-light OLED dopant material, but also have extremely high luminous performance, with a quantum yield of 96% and 100%, respectively.

Example 15

Preparation of compound (II-3-4):

(II-3-4)

Except that the starting reactants were different, the synthesis steps were similar to those of compound (II-3-1), with a yield of 65%.

Spectrum data of compound (II-3-4): MS (FAB, $^{195}$Pt): m/z 705 [M$^+$]; $^1$H NMR (500 MHz, d$_6$-DMSO 294K): δ 7.72 (d, J=2.0 Hz, 2H), 7.71 (d, J=2.0 Hz, 2H), 6.23 (d, J=13.0 Hz, 1H), 6.15 (d, J=13.0 Hz, 1H), 5.13 (sp, J=6.5 Hz, 2H), 1.63 (d, J=6.5 Hz, 6H), 1.19 (d, J=6.5 Hz, 6H); $^{19}$F NMR (470 MHz, d$_6$-DMSO, 294K): δ -63.18 (s, 6F).

Accordingly, in the invention, strong-field carbene chelates having carbon as bonding atoms are used. In addition to having a vacant orbital of a higher energy and causing a blue shift to the emission wavelength, these chelates can also effectively increase the d-d orbital transition energy level of the complex, such that the Pt complex still has good blue-light or green-light luminous efficiency when molecules are stacked. Moreover, the luminous light color can be adjusted by functional group modification on the chelates, and the rigidity can be increased by forming an intra-molecular hydrogen bond. Therefore, the quantum yield can reach up to 100%. Moreover, by changing the number of carbon atoms of the alkyl group of the carbene, the sublimability of the compound can be increased, and with the property of short phosphorescence lifetime, occurrence of triple-state quenching can be reduced, thus sufficiently improving the performance of the element.

Although the invention has been described with reference to the above embodiments, it will be apparent to one of ordinary skill in the art that modifications to the described embodiments may be made without departing from the spirit of the invention. Accordingly, the scope of the invention is defined by the attached claims not by the above detailed descriptions.

What is claimed is:

1. A platinum complex having a carbene fragment, containing: a platinum cation, a zero-valent first nitrogen-containing heterocyclic bidentate chelate, and a dianionic second nitrogen-containing heterocyclic bidentate chelate, wherein the first nitrogen-containing heterocyclic bidentate chelate has at least one carbene unit coordinating to platinum, and the second nitrogen-containing heterocyclic bidentate chelate has at least one electron-withdrawing substituent and forms two N—Pt bonds, or one N—Pt bond and one C—Pt bond, with the platinum cation,
wherein the platinum complex is represented by formula (I) or (II):

wherein X is CH or N, $R^F$ is —$C_mF_{2m+1}$ and m is an integer of 1 to 7.

2. The platinum complex of claim 1, wherein the first nitrogen-containing heterocyclic bidentate chelate is represented by formula (1), (2) or (3):

wherein $R^1$ is hydrogen, $C_{1-12}$ alkyl, unsubstituted phenyl, or a substituted phenyl group, each $R^2$ is independently $C_{1-6}$ alkyl, each $R^3$ is independently hydrogen, $C_{1-12}$ alkyl, unsubstituted phenyl, or a substituted phenyl group, $R^4$ is hydrogen or $C_{1-6}$ alkyl, and n is 1, 2 or 3, wherein any two adjacent $R^3$ may join to form a ring.

3. The platinum complex of claim 2, which is represented by formula (I-1-1), (I-1-2), (I-1-3), (I-1-4), (I-1-5) or (I-1-6):

(I-1-1)

(I-1-2)

(I-1-3)

(I-1-4)

(I-1-5)

(I-1-6)

4. The platinum complex of claim 2, which is represented by formula (II-2-1), (II-2-2), (II-2-3), (II-2-4), (II-2-5), (II-2-6), (II-2-7), (II-2-8), (II-2-9) or (II-2-10):

(II-2-1)

(II-2-2)

(II-2-3)

(II-2-4)

(II-2-5)

5. The platinum complex of claim 2, which is represented by formula (II-3-1), (II-3-2), (II-3-3), (II-3-4), (II-3-5) or (II-3-6):

6. An organic light-emitting diode, comprising two electrodes and a light-emitting layer disposed between the two electrodes, wherein the light-emitting layer contains the platinum complex of claim 1.

* * * * *